United States Patent [19]

Brown et al.

[11] 4,374,731
[45] Feb. 22, 1983

[54] METHOD AND APPARATUS FOR OBTAINING A DESIRED RATE OF PLASMA COLLECTION FROM A MEMBRANE PLASMAPHERESIS FILTER

[75] Inventors: Richard I. Brown, Northbrook; Arnold C. Bilstad, Deerfield, both of Ill.

[73] Assignee: Baxter Travenol Laboratories, Inc., Deerfield, Ill.

[21] Appl. No.: 127,733

[22] Filed: Mar. 6, 1980

[51] Int. Cl.³ .................... B01D 31/00; B01D 13/00
[52] U.S. Cl. .................................... 210/637; 210/90; 210/351; 210/433.2
[58] Field of Search .............. 210/650, 137, 344, 351, 210/356, 433.2, 321, 927, 456, 90, 418, 321.3, 321.5, 232, 236, 637

[56] References Cited

U.S. PATENT DOCUMENTS

| | | | |
|---|---|---|---|
| 1,197,403 | 9/1916 | Seavey | 210/351 |
| 3,342,328 | 9/1967 | Swenson | 210/321.5 X |
| 3,352,421 | 11/1967 | Cary | 210/321.3 X |
| 3,495,566 | 2/1970 | Pall | 210/90 |
| 3,528,554 | 9/1970 | Ogden et al. | 210/347 |
| 3,579,441 | 5/1971 | Brown | 210/434 |
| 3,695,445 | 10/1972 | Esmond | 210/321.3 |
| 3,705,100 | 12/1972 | Blatt et al. | 210/321.1 |
| 4,013,564 | 3/1977 | Nose | 210/434 |
| 4,191,182 | 3/1980 | Popovich et al. | 210/433.2 |
| 4,228,015 | 10/1980 | DeVries et al. | 210/434 |
| 4,243,532 | 1/1981 | Tsudu et al. | 210/434 |

*Primary Examiner*—Frank A. Spear, Jr.
*Attorney, Agent, or Firm*—Paul C. Flattery; George H. Gerstman; Daniel D. Ryan

[57] ABSTRACT

A method and apparatus are described for obtaining a desired rate of plasma collection from a membrane plasmapheresis filter having a blood inlet, a blood outlet, a plasma outlet, outer members and a pair of spaced microporous filter membranes defining a blood flow path. A holder is provided for the filter having means for applying pressure against the outer members. The blood pressure at the blood inlet is sensed during plasmapheresis and variable amounts of pressure are applied against the outer members at an angular direction with respect to the membranes. In this manner, the blood flow path gap between the membranes is controlled in accordance with a desired blood pressure adjacent the blood inlet.

9 Claims, 4 Drawing Figures

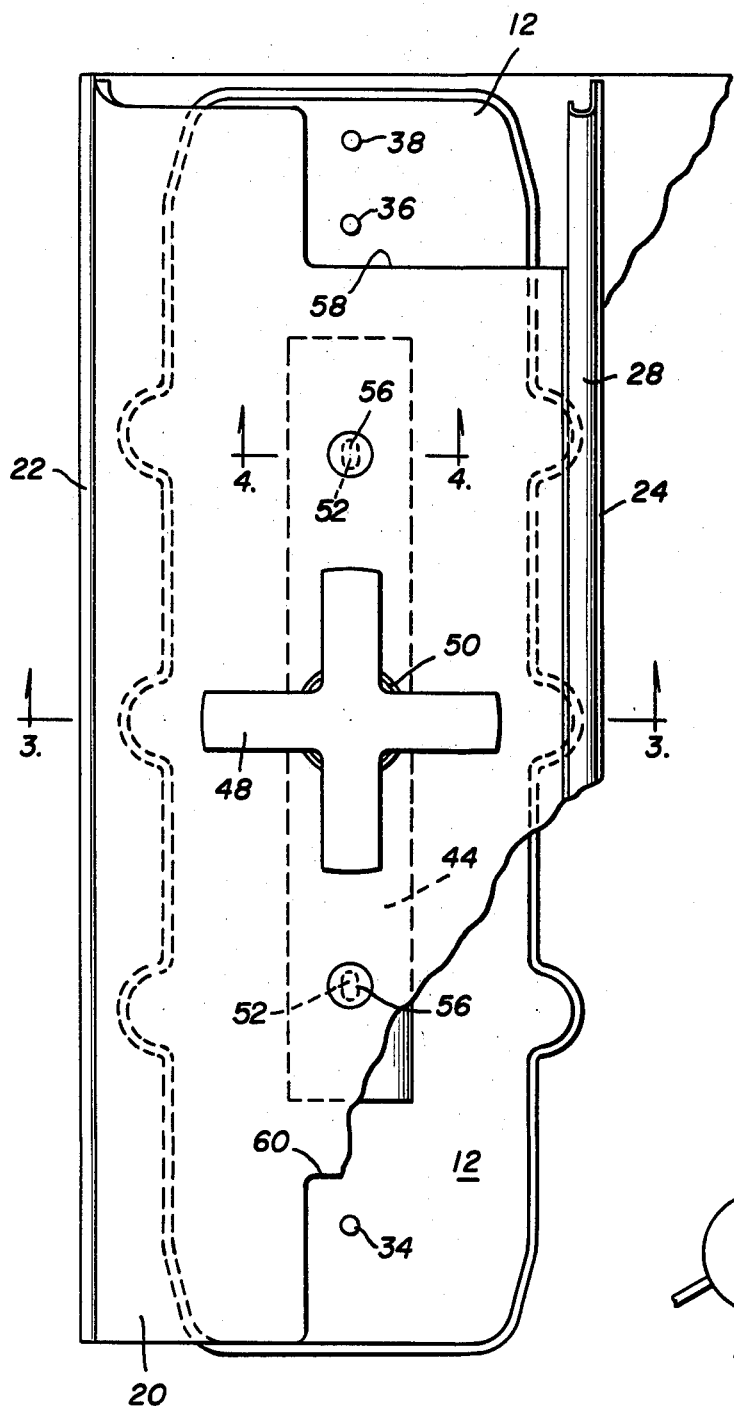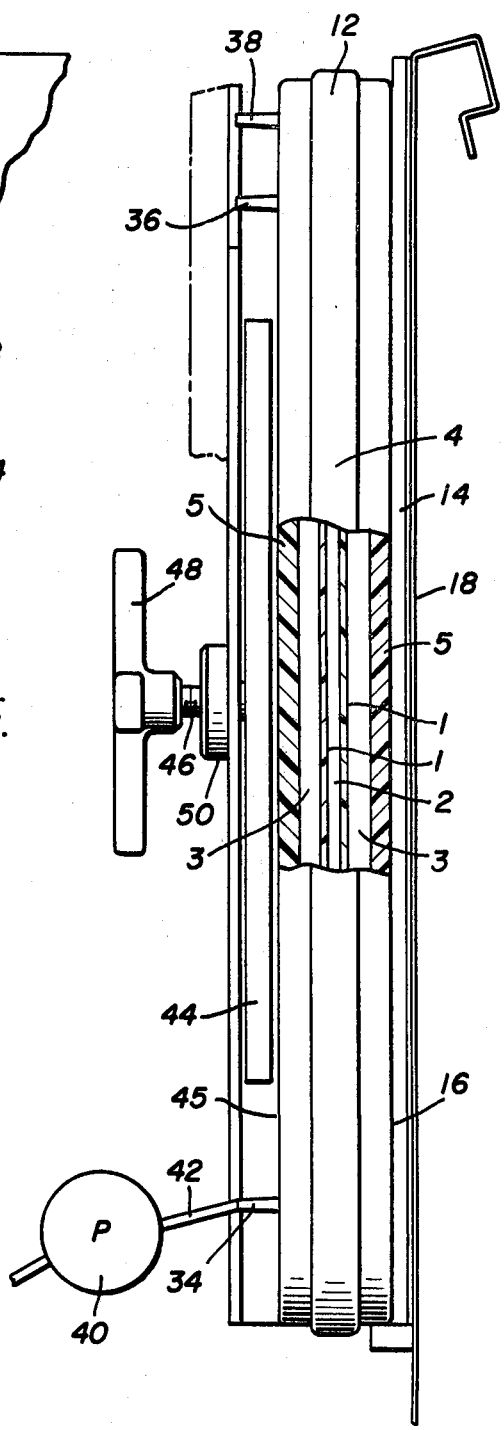

METHOD AND APPARATUS FOR OBTAINING A DESIRED RATE OF PLASMA COLLECTION FROM A MEMBRANE PLASMAPHERESIS FILTER

BACKGROUND OF THE INVENTION

The present invention concerns a novel method and apparatus for obtaining a desired rate of plasma collection from a membrane plasmapheresis filter.

In plasmapheresis, plasma is extracted from whole blood taken from a donor and the plasma is collected with the red cells being returned to the donor. Although extraction of plasma by centrifugation has been widely used, membrane plasmapheresis has recently been found to be very effective and more desirable in certain circumstances.

In membrane plasmapheresis, the whole blood is filtered through a microporous membrane having a pore size to pass the plasma filtrate but blocking the cellular material which remains on the upstream side of the microporous membrane. In abandoned U.S. patent application Ser. No. 942,077, filed Sept. 13, 1978, in the names of James H. DeVries, Ludwig Wolf, Jr., Gaylor Berry and William J. Schnell, and entitled "Apparatus for Membrane Plasmapheresis", a membrane plasmapheresis filter cell 12 is disclosed, as shown in FIGS. 2 and 3 of the instant application. The filter cell 12 includes a pair of generally parallel filter membranes 1 defining a blood flow path 2 therebetween, a pair of plasma filtrate volumes 3 defined on the opposite sides of the membranes 1 from the blood flow path 2, an outer casing 4 surrounding the membranes 1 and plates 5 supporting the membranes 1, a blood inlet 34 communicating with the blood flow path 2, a blood outlet 36 communicating with the blood flow path 2, and a plasma outlet 38 communicating with the plasma filtrate volumes 3. We have discovered that during plasmapheresis, the blood flow path gap 2 between the microporous membranes 1 tends to increase, thereby lowering the transmembrane blood pressure resulting in a decreased plasma collection rate. We have also discovered that an optimum plasma collection rate can be calculated by first determining the maximum whole blood flow rate desired (with the physical factors of the donor taken into consideration for this determination) then determining the inlet blood pressure to the membrane plasmapheresis filter cell which will result in this maximum whole blood flow rate, and then maintaining this inlet blood pressure during plasmapheresis to obtain a desired rate of plasma collection. As an example, a doctor would decide how much flow rate of blood he can safely obtain from a donor. The total whole blood flow rate is a combination of the blood taken from the donor and also the blood infused by recirculation. The doctor may set up a rate, for example, 250 ml per minute, and then by graphical determination, the doctor can determine what blood pressure at the filter cell inlet is necessary to obtain a desired plasma collection rate. Since the plasma collection rate is generally proportional to the inlet blood pressure at a particular whole blood flow rate, by increasing the inlet blood pressure a greater plasma collection rate can be achieved.

It is, therefore, an object of the present invention to provide a method for obtaining a desired rate of plasma collection, by maintaining the blood flow gap between the membranes.

Another object of the present invention is to provide a method for obtaining a desired plasma collection, using a pair of membranes and adjustable means to maintain the blood flow path gap.

A further object of the present invention is to provide apparatus for maintaining a desired blood film thickness between the membranes of a membrane plasmapheresis cell, by forcing the cell in a manner so that the film thickness remains constant as desired.

A still further object of the present invention is to provide a method and apparatus for obtaining a desired rate of plasma collection from a membrane plasmapheresis filter cell, by measuring the blood inlet pressure to the cell and maintaining the blood inlet pressure constant.

Other objects and advantages of the present invention will become apparent as the description proceeds.

SUMMARY OF THE INVENTION

In accordance with the present invention, a method is provided for obtaining a desired rate of plasma collection from a membrane plasmapheresis filter having a blood inlet, a blood outlet, a plasma outlet, outer members and a pair of spaced microporous filter membranes defining a blood flow path therebetween. A holder is provided for the filter having means for applying pressure against the outer members. The blood pressure adjacent the blood inlet is sensed during plasmapheresis, and variable amounts of pressure are applied against the outer members at an angular direction with respect to the membranes. In this manner, the blood flow path gap between the membranes is controlled in accordance with a desired blood pressure adjacent the blood inlet.

In accordance with the present invention, apparatus is provided for regulating the blood pressure in the membrane plasmapheresis filter. A housing is provided for receiving the filter with the housing comprising a back panel for supporting a back side of the filter, and a front panel is coupled to the back panel. The front panel includes means for applying pressure against a front side of the filter. The pressure applying means comprises an adjustable member for urging the front side toward the back side. Means are coupled to the blood inlet for sensing the blood pressure. The adjustable member is operative to control the blood flow path gap between the membranes in accordance with a desired blood pressure at the blood inlet.

In the illustrative embodiment, the adjustable member comprises an elongated pressure member extending in the longitudinal direction of the filter. A screw is connected to the pressure member and a manually operable screw handle is connected to the screw. Turning the screw handle in respective directions increases and decreases the pressure of the pressure member against the front side of the filter.

A more detailed explanation of the invention is provided in the following description and claims, and is illustrated in the accompanying drawings.

BRIEF DESCRIPTION OF THE DRAWINGS

FIG. 1 is a front view of an apparatus for obtaining a desired rate of plasma collection from a membrane plasmapheresis filter, constructed in accordance with the principles of the present invention and showing a filter in dashed lines, with portions of the apparatus broken away for clarity;

FIG. 2 is a side elevational view thereof;

DETAILED DESCRIPTION OF THE ILLUSTRATIVE EMBODIMENT

Figure 3:
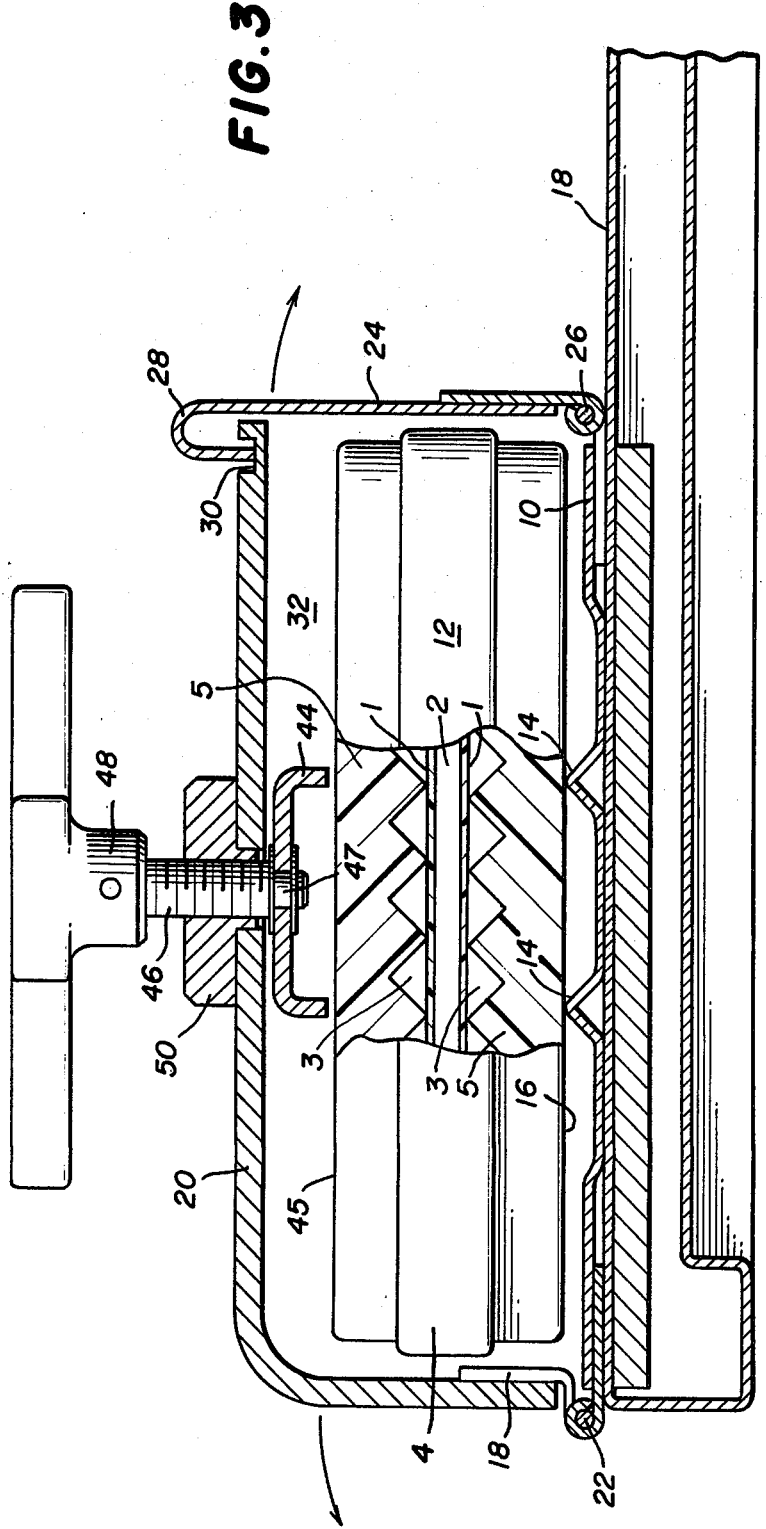
FIG. 3 is a cross-sectional view thereof, taken along the plane of the line 3—3 of FIG. 1.

Referring to the drawings, the apparatus comprises a housing having a back panel 10 which supports the filter cell 12 by means of longitudinal ridges 14 which extend the length of back panel 10 and are adapted to engage the back side 16 of the outer casing of filter cell 12. Back panel 10 is attached to a support 18 by suitable fastening means or by welding, and support 18 may comprise a panel of a membrane plasmapheresis apparatus.

A hinge 19 is connected to back panel 10 and is fastened by welding or other suitable connecting means to a front panel 20. Thus front panel 20 is adapted for pivoting about pivot pin 22. A latch plate 24 is pivotally connected to back panel 10 by means of a pivot pin 26, with latch plate 24 having a bend 28 which is resiliently coupled to front panel 20 by entering it into a slot 30 defined by front panel 20.

Front panel 20, latch plate 24 and back panel 10 define an open volume 32 for receiving filter cell 12. When filter cell 12 is to be inserted or removed from the housing, resilient bend 28 is pulled out of slot 30 and moved clockwise (with respect to FIG. 3) about pin 26, and front panel 20 is then moved counterclockwise (with respect to FIG. 3) about pin 22.

As illustrated in FIG. 2, filter cell 12 has a blood inlet 34, a blood outlet 36 and a plasma filtrate outlet 38. A blood pressure transducer 40 is coupled in series with line 42 adjacent blood inlet 34, to sense the blood inlet pressure.

A pressure applying member 44, in the form of an elongated channel having a generally U-shaped cross-sectional configuration, is provided. This pressure channel 44 may be adjustably forced against the front side 46 of a casing of filter cell 12, the pressure adjusting means comprises a screw 46 having one end 47 fixed to channel 44 and its other end keyed to a manually operable screw handle 48. The screw 46 is journaled within a hub 50 which is fastened to front plate 20. It can be seen that rotation of handle 48 in a first direction moves channel 44 toward back panel 10, to apply pressure to the outer casing of filter cell 12. Manual turning of the handle 48 in the opposite direction moves pressure channel 44 away from back panel 10. As shown in FIGS. 1 and 2, pressure channel 44 is elongated and extends longitudinally with respect to the filter cell 12.

Figure 4:
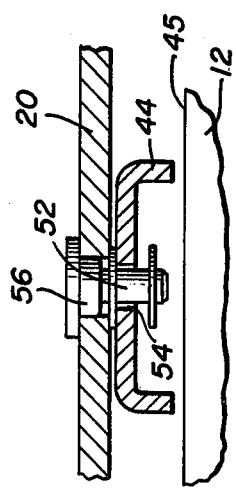
FIG. 4 is a fragmentary cross-sectional view thereof, taken along the plane of the line 4—4 of FIG. 1.

In order to prevent the pressure channel 44 from rotating during rotation of handle 48, a pair of restraining pins 52 (FIGS. 1 and 4) extend through apertures 54 of pressure channel 44 and are fastened by a cap member 56 to front panel 20. The front panel has cut-away portions 58 and 60 (FIG. 1) to permit easy access to inlet 34 and outlets 36, 38.

It can be seen that the housing described herein serves to provide a clamping arrangement as a part of a membrane plasmapheresis machine, to adjust the blood flow path gap between the membranes. In this manner, the blood flow path gap may be controlled in accordance with a desired blood pressure at the inlet 34. The casing of filter cell 12 may be formed of a semi-rigid plastic material which has sufficient flexibility to compress the membranes when pressure channel 44 is urged into pressure contact with surface 45.

Although an illustrative embodiment of the invention has been shown and described, it is to be understood that various modifications and substitutions may be made by those skilled in the art without departing from the novel spirit and scope of the present invention.

What is claimed is:

1. A method for obtaining a desired rate of plasma collection from a membrane plasmapheresis filter having a pair of spaced microporous filter membranes defining therebetween a blood flow path which has spaced inlet and outlet ends and which expands in cross section during blood flow therethrough, which method comprises the steps of:

establishing a flow of blood between the inlet and outlet ends of the blood flow path, applying pressure against and at substantially a perpendicular direction with respect to the membranes essentially along the entire axial length of the blood flow path between the inlet and outlet ends thereof to establish the spacing between the membranes to develop at the inlet end of the blood flow path a blood pressure preselected to achieve a desired transmembrane pressure, and continuously maintaining the pressure essentially along the entire axial length of the blood flow path to prevent a subsequent expansion of the blood flow path in cross section during the plasmapheresis procedure and to thereby maintain the desired blood inlet pressure.

2. Apparatus for obtaining a desired rate of plasma collection from a membrane plasmapheresis filter having a pair of substantially parallel, spaced microporous filter membrane defining a blood flow path therebetween, a blood inlet and a blood outlet longitudinally spaced along and communicating with the flow path, a plasma outlet, and first and second generally flexible outer members extending outwardly of and generally parallel to the membranes to sandwich the membranes therebetween, said apparatus comprising:

a housing for receiving the filter and comprising a first panel including means for supporting the first generally flexible outer member essentially along the entire axial length of the blood flow path when the filter is received in said housing and a second panel coupled to said first panel and facing the second generally flexible outer member when the filter is received in said housing;

said second panel including means for selectively applying pressure against the second generally flexible outer member essentially along the entire axial length of the blood flow path to urge the second generally flexible outer member toward the first generally flexible outer member supported by said first panel and establish and thereafter maintain the desired spacing between the membranes, whereby a desired blood pressure can be achieved and maintained at the blood inlet of the filter to obtain the desired rate of plasma collection during the plasmapheresis procedure.

3. An apparatus according to claim 2
wherein said housing includes hinge means coupling said second panel to said first panel and means spacing said second panel from said first panel to provide a volume within said housing for receiving the filter.

4. An apparatus according to claim 2 or 3
wherein said pressure application means comprises an elongated pressure member extending in the longitudinal direction between the blood inlet and blood outlet of the filter and engagable against the second outer member, and screw means operatively connected with said pressure member for rotation in a first direction increasing the pressure of said pressure member against the engaged side of the filter to decrease the spacing between the membranes and for rotation in a second direction decreasing the pressure of said pressure member against the engaged side of the filter to increase the spacing between the membranes.

5. An apparatus according to claim 4 wherein said adjustable member includes means for restricting rotational movement of said elongated pressure member relative to the filter during rotation of said screw means.

6. An apparatus according to claim 5, wherein said rotational movement restricting means comprising pin means connected to said second panel and engaging said pressure member.

7. An apparatus according to claim 6, wherein said pressure member comprises a channel-shaped member having a generally U-shaped cross-sectional configuration.

8. An apparatus according to claim 4 wherein said support means on said first panel includes spaced ridge means extending continuously along said first panel for engaging the first generally flexible outer member essentially along the entire axial length of the blood flow path in opposition to said elongated pressure member engaging the second generally flexible outer member when the filter is received in said housing.

9. An apparatus according to claim 2 and further including means coupled to the blood inlet of the filter for sensing the blood pressure at the inlet.

* * * * *